United States Patent [19]

Blanco-Esteve

[11] Patent Number: 5,801,058
[45] Date of Patent: Sep. 1, 1998

[54] ANALYTIC METHOD TO DETERMINE THE FERTILIZING CAPACITY OF A HUMAN SEMEN SAMPLE

[76] Inventor: Carmen Blanco-Esteve, Martín El Humano, 1—pta. 22, 46008 Valencia, Spain

[21] Appl. No.: 799,892

[22] Filed: Feb. 13, 1997

Related U.S. Application Data

[63] Continuation of Ser. No. 489,948, Jun. 13, 1995, abandoned.

[30] Foreign Application Priority Data

Jun. 20, 1994 [ES] Spain ............................ 9401341

[51] Int. Cl.$^6$ ............................................ G01N 33/48
[52] U.S. Cl. ..................... 436/63; 436/166; 436/174; 436/906; 422/61; 435/29; 435/806; 435/810
[58] Field of Search .................. 436/63, 65, 166, 436/174, 814, 906; 422/61; 435/806, 810, 29; 424/561

[56] References Cited

U.S. PATENT DOCUMENTS

| | | | |
|---|---|---|---|
| 4,329,337 | 5/1982 | Sexton | 424/561 |
| 4,767,703 | 8/1988 | Ax et al. | 435/29 |
| 4,804,537 | 2/1989 | Bergman et al. | 424/561 |
| 5,358,847 | 10/1994 | Brown | 435/6 |
| 5,474,890 | 12/1995 | Di Virgilio et al. | 435/1.1 |

FOREIGN PATENT DOCUMENTS

| | | |
|---|---|---|
| 2044778 | 1/1994 | Spain . |
| 917838 | 4/1982 | U.S.S.R. . |
| 980706 | 12/1982 | U.S.S.R. . |
| 1676614 | 9/1991 | U.S.S.R. . |

OTHER PUBLICATIONS

Singer et al. (1982) Int. J. Fertil. 27(3):176–80.
Princewill et al. (1972) Med. Lab. Technol. 29:255–60.
Huszar et al. (1990) Fertil. Steril. 54:1127–34.
Guillet-roso et al. (1987) Brit. J. Obst. Gynecol. 94:543–7.
Talbert et al. (1987) Fertil. Steril. 48:270–7.
Ziegler et al. (1987) Fertil. Steril. 48:816.
Madaheva et al. (1984) Fertil. Steril. 42:400–5.
Singer et al. (1983) Int. J. Fertil. 28:119–20.
Jedendrau et al. (1984) J. Reprod. Fertil. 70:219–218.
Yushhenko (1976) CA Abst. No. 86:85785 (SU 536824).
Hirayama et al. (1989) Fert. Steril. 51:330–4 (Medline Abst.).
Sexton et al. (1978) Poulty Sci. 57:277–84.

*Primary Examiner*—Maureen M. Wallenhorst
*Attorney, Agent, or Firm*—Klauber & Jackson

[57] ABSTRACT

The invention relates to improvements in determining the fertilizing capacity of a human semen sample using a reagent solution which contains 0.1–5% by weight $K_2PO_4H/KPO_4H_2$ to adjust the pH of the solution to 6.5–8.0. After treatment with the reagent solution, the result is considered positive when the diameter of the halo is equal to or larger than 7.5μ in 10–25% of the spermatozoa read, as long as the membrane of the head of the spermatozoon is intact. Kits suitable for performance of the claimed method are also described.

5 Claims, No Drawings

ANALYTIC METHOD TO DETERMINE THE FERTILIZING CAPACITY OF A HUMAN SEMEN SAMPLE

This Application is a Continuation of application Ser. No. 08/489,948, filed Jun. 13, 1995 now abandoned.

TECHNICAL FIELD OF THE INVENTION

The present invention refers to an improved analytic method to determine the fertilizing capacity of human and animal semen samples and to a kit used to make said determination easier.

PRIOR ART OF THE INVENTION

In human reproduction, one of the most important problems from the social and clinical point of view is sterility in a couple and the study of the pathology that causes it.

A couple is considered to be sterile from the clinical point of view, when at least two years have gone by since they live together and no pregnancy has been caused, when, of course, no method to prevent it has been used.

Normally, the medical study of sterility in a couple is done on both spouses at the same time for the purpose of adequately diagnosing the cause.

Sterility in a couple may be a result of the male, female or both of them.

It is known that sterility in males is the cause of sterility of a couple in 40–50% of the cases.

In certain circumstances it is possible to overcome the reasons of sterility with suitable medical treatment, however, in other circumstances it is necessary to resort to artificial reproduction (AR) techniques. These techniques have developed at a world-wide level and they are basically artificial insemination (AI) and in vitro fertilization (IVF.)

In general terms, semen is considered not to be normal (normospermic) when its count is lower than 20 million spermatozoa per mL, the linear and progressive motility thereof is less than 40% and it has more than 50% anormal shapes. Semen with these characteristics encounters difficulties for natural fertilizing, which makes it necessary to resort to one of the above mentioned artifical reproduction techniques. Specifically, one of the treatments most selected would be IVF (in vitro fertilization).

As is well known, the results of these techniques have a relatively low percentage of success, in the neighborhood of 20–40%, non-fertilization by the spermatozoon being the first cause of failure.

Normally, some parameters that allow one to determine a priori if the semen is going to be capable of in vitro fertilizing or not are determined, observing in practice that semen with theoretically "good" parameters is not capable of in vitro fertilization and another semen with "worse" parameters, however, can cause fertilization.

Therefore, there is still a problem that is unresolved with regard to said parameters, in such a way that the parameters that presently exist do not suffice to diagnose the fertilizing capacity of semen.

Along these lines and for the purpose of being able to potentially avoid failure, at times repetitive, in the in vitro fertilization techniques due to the quality of the semen, the present invention provides an analytic method to determine the fertilizing capacity of a human semen sample that allows one to determine a priori if said semen is going to be capable of fertilizing the oocytes of his partner in vitro or not, thus avoiding, on the one hand, disenchantment and disillusionment of the couple and, on the other hand, unnecessary expenses since this technique is very expensive.

Up to now, the importance of the viability of human semen has been considered with a view to its fertilizing capacity. But it need not even be said how important this matter may become in the veterinary field, where suitable reproduction of livestock may have extensive repercussions at the economic-industrial level.

As bibliographic references related to the object of the present invention, the following ones may be cited:

1. SINGER R. SAGIV M. ALLALOUF D. ET AL., Lack of Correlation between Acrosomal Pathologies of Human Spermatozoa and Hyaluronidase Activity: Int. J. Fertil. 1983, 28(2): 119–120.

2. HUSZAR G. WILLETS M. CORRALES M., Hyaluronic acid (Sperm Select) improves retention of sperm motility and velocity in normospermic cno. Fertility Sterility 1990, 54(6): 1127–34.

3. GUILLET-ROSO F. FARI A. TAYLOR A. FORMAN R. ET AL., Systematics semen culture and its influence on I.V.F., management., Brit. J. Obst. Gynecol. 1987, 94: 543–547.

4. JEDENDRAU R. AND VAN DER VAN H., Development of an assay to assess the functional integrity of the human sperm membrane and its relati. J. Reprod. Fertil. 1970, 70: 219–218.

5. MADAHEVA M. TROUNSON A., The influence of seminal characteristics on the success rate of human in vitro fertilization. Fertil. Steril. 1984, 42:400–405.

6. TALBERT L. HAMMOND M. HOLME J. ET AL., Semen parameters and fertilization of human oocytes in vitro, a multivariable analysis, Fertil. Steril. 1987, 48: 270–277.

7. ZIEGLER D. CEDARS M. HAMILTON F. MORENO T., MELDRUM Y., Factor influencing maintenance of sperm motility during in vitro processing. Fertil. Steril. 1987, 48–816.

Besides, the applicant herself in ES Patent no. 2,044,778 proposes a method to determine the fertilizing capacity of a human semen sample that has implied a great technical advancement given its simplicity and reliability.

However, the applicant continuing her scientific studies regarding the matter has improved said method, at the same time that she has verified its viability on animal semen. Likewise, she has designed a kit whose purpose is to facilitate the carrying out of said method.

DETAILED DESCRIPTION OF THE INVENTION

The present invention refers to improvements of Spanish patent no. 2,044,778.

This patent referred to an analytic method to determine the fertilizing capacity of a human semen sample that is carried out in vitro, a normal standardized procedure in laboratories.

Said analytic method is based on putting, under certain conditions, a solution formulated with some active principles, in contact with the semen sample, causing a reaction in which an enzyme that is found in the inside of the membrane of the head of the spermatozoon is released, which gives rise to areas of digestion (halo) on the substrate, around said head of the spermatozoon once said enzyme is released, the head of the spermatozoon must remain thickened and with its outside membrane intact and produce a diameter of the halo of digestion on the substrate larger than 7.5μ, there being a correlation between the size of said halo and the capacity that that spermatozoon has to fertilize or not to fertilize.

The composition of said solution is the following:
0.5–10% by weight of hyaluronic acid
20–90% by weight of calcium chloride 5 mM
0.1–5% of Triton X Specifically, the analytic method claimed in patent no. 2,044,778 is characterized by the following operations:

a) taking a drop of the cited solution and spreading it on a slide, letting it dry for 1–2 minutes;

b) taking a previously washed and adapted semen sample and spreading it on the slide previously impregnated with the solution according to step (a); covering it with a coverglass and letting it incubate for 30 minutes to 48 hours approximately at about 25°–40° C. in an incubator with about 1%–10% $CO_2$;

c) evaluating the results by means of reading, under a phase contrast microscope coupled to the eyepiece with a magnifying power of 10–40, of the halo formed and of the size of its diameter.

This method of analysis is considered positive, in other words, that the semen analyzed is capable of fertilizing, if the diameter of the halo is equal to or larger than 7.5μ in at least 50% of the spermatozoa read. It is considered that the result is negative for lower values or when there is no halo.

Now, the applicant has introduced some improvements in the analytic technique whose purpose is:

1.) to stabilize the reactive solution used in the analysis; and

2.) an interpretation of the results to perfect as much as possible the value of the data obtained.

Besides, the applicant has designed a kit to facilitate the practical carrying out of the analytic method.

Finally, the applicant has been able to verify, by means of the corresponding studies, that the method is likewise applicable to animal semen samples.

The reactive solution used in the process of patent no. 2,044,778 and comprised of: 0.5–15% by weight of hyaluronic acid; 20–90% by weight of calcium chloride 5 mM and 0.1–5% of Triton, is not very stable with a view of its possible marketing to carry out the analysis on an industrial scale.

To achieve the increase of stability of the cited reactive solution during prolonged periods of time, comprised between 6 months and 1 year, the applicant has discovered that it suffices to add to the same $K_2PO_4H/KPO_4H_2$ in proportions between 0.1 and 5% by weight and, besides, the pH of the cited solution must be adjusted between 6.5 and 8.0.

On the other hand, in the process of patent no. 2,044,778, in the final stage of interpreting the results, it was considered that the result was positive (in other words, that the semen analyzed was capable of fertilizing) if the diameter of the halo was equal to or larger than 7.5μ in at least 50% of the spermatozoa read.

Now, the applicant has been able to verify that the result is likewise positive when the cited diameter of the halo is equal to or larger than 7.5μ in 10–25% only of the spermatozoa read, as long as the membrane of the head of the spermatozoon remains intact.

Besides, the applicant has designed a commercial kit whose purpose is to facilitate the carrying out of the trials and tests corresponding to the analytic method of the present invention. Said kit is characterized in that it is comprised of:

(1) a syringe provided with a stopper or a dropper bottle with the stabilized reactive solution already described above;

(2) a glass slide for the microscope and a coverglass, which are included in said kit in a suitable amount so that all of the reagent can be used, taking into account that for each drop of solution one slide and one coverglass are required;

(3) disposable pipets to apply the drop of semen to be analyzed.

EMBODIMENTS OF THE INVENTION

The present invention is additionally illustrated by means of the following non-restrictive examples of its scope, which is defined solely and exclusively by the attached set of claims.

EXAMPLE 1

The following analytic method was carried out:

1.) A drop of recently prepared solution containing 7% hyaluronic acid, 60% calcium chloride 5 mM, 2.5% Triton X and 6% $K_2PO_4H/KPO_4H_2$, whose pH had been adjusted to 7 was taken and spread on a slide, letting it dry for 5 minutes;

2.) 0.5 μl of a previously washed and adapted human semen sample were taken and spread on the slide previously impregnated with said solution. It was covered with a coverglass and incubated for 24 hours at 37° C. in an incubator with 5% $CO_2$.

3.) The result was evaluated by reading under a phase contrast microscope with a micrometer coupled to the eyepiece with a magnifying power of 40.

4.) A diameter of the halo formed around the head of the spermatozoon of 8μ was observed, the membrane of the head of the spermatozoon remaining intact in 20% of them. Therefore, the result was considered as being positive. This result was contrasted with the result obtained with the same in vivo semen sample by means of the IVF technique where the oocytes obtained in the partner were fertilized.

EXAMPLE 2

The method described in Example 1 was carried out, but using a solution that was prepared one year before, obtaining the same result.

EXAMPLE 3

The method described in Example 1 was carried out, but using a breeding bull semen sample.

It was observed that the diameter of the halo formed around the head of the spermatozoon was 8.2μ the membrane of the head of the spermatozoon remaining intact in 22% of them. Therefore, the result was considered positive.

EXAMPLE 4

The method described in Example 3 was carried out, but using a solution that was prepared 14 months before, obtaining exactly the same result.

CLARIFICATION

All the results considered as examples were simultaneously contrasted with the IVF technique to which the couples were subjected; verifying the results obtained in vivo.

I claim:
1. An analytical method for determining the fertilizing capacity of a semen sample comprising:
   a) a first step which comprises spreading a drop of reagent solution comprised of 0.5–15% by weight of hyaluronic acid, 20–90% by weight of 5 mM calcium chloride, 0.1–5% by weight of Triton X and 0.1–5% by weight of a potassium phosphate selected from the group consisting of potassium mono-phosphate, potassium diphosphate and mixtures thereof, onto a microscope slide, and allowing the reagent solution to dry for 1–2 minutes, wherein said reagent solution has a pH between 6.5 and 8.0;
   b) a second step which comprises spreading a previously washed semen sample on said slide; covering said slide with a coverglass and allowing said slide to incubate for 30 minutes to approximately 48 hours at about 25°–40° C. in an incubator with about 1%–10% carbon dioxide to obtain an incubated sample;
   c) a third step which comprises reading, under a phase contrast microscope having an eyepiece with a micrometer, halos formed around heads of spermatozoa in said incubated sample and evaluating a size of the diameter of said halos;
   d) a fourth step which comprises assessing a fertilizing capacity of said incubated sample by determining if between 10–25% of the spermatozoa heads with intact head membranes have halo diameters equal to or larger than 7.5 microns, whereby this level indicates a positive capability of fertilization.

2. A kit for use in the method according to claim 1 which comprises:
   (1) a syringe provided with a stopper or a dropper bottle capable of dispensing drops of said reagent solution;
   (2) glass slides for said microscope and coverglasses therefor which are included in said kit in a sufficient amount so as to provide sufficient slides and coverglasses for an amount of reagent solution taking into account that for each drop of reagent solution, one slide and one coverglass are required;
   (3) disposable pipets to apply a drop of semen to be analyzed to said glass slides; and (4) a quantity of stabilized reagent solution comprising
   0.5–15% by weight of hyaluronic acid,
   20–90% by weight of 5 mM calcium chloride,
   0.1–5% by weight of Triton X, and
   0.1–5% by weight of a potassium phosphate selected from the group consisting of potassium monophosphate, potassium diphosphate and mixtures thereof which results in said reagent solution having a pH between 6.5 and 8.0.

3. An analytical method according to claim 1 wherein the semen sample is human.

4. An analytical method according to claim 1 wherein the reagent solution comprises 7% hyaluronic acid, 60% 5 mM calcium chloride, 2.5% Triton X and 6% of a potassium phosphate selected from the group consisting of potassium mono-phosphate, potassium diphosphate and mixtures thereof.

5. An analytical method according to claim 1 wherein the second step is conducted at 37° C. in an incubator with 5% carbon dioxide.

* * * * *